United States Patent [19]
Salek et al.

[11] Patent Number: 5,532,417
[45] Date of Patent: * Jul. 2, 1996

[54] MANUFACTURE OF NEOPENTYL GLYCOL (IV)

[75] Inventors: Jeffrey S. Salek, Oakdale Boro; Joseph Pugach, Monroeville Boro; Carole L. Elias, Allegheny County; Leonard A. Cullo, Greensburg, all of Pa.

[73] Assignee: Aristech Chemical Corporation, Pittsburgh, Pa.

[*] Notice: The portion of the term of this patent subsequent to Sep. 1, 2009, has been disclaimed.

[21] Appl. No.: 100,356

[22] Filed: Aug. 2, 1993

Related U.S. Application Data

[63] Continuation of Ser. No. 894,961, Jun. 8, 1992, abandoned, which is a continuation-in-part of Ser. No. 723,097, Jun. 28, 1991, Pat. No. 5,146,012, which is a continuation-in-part of Ser. No. 691,927, Apr. 26, 1991, Pat. No. 5,144,088, and a continuation-in-part of Ser. No. 716,177, Jun. 17, 1991, abandoned.

[51] Int. Cl.$^6$ ............ C07C 29/14; C07C 45/45; C07C 31/20
[52] U.S. Cl. ............ 568/853; 568/464; 568/862
[58] Field of Search ............ 568/464, 862, 568/853

[56] References Cited

U.S. PATENT DOCUMENTS

| | | | |
|---|---|---|---|
| 3,808,280 | 4/1974 | Merger et al. | 260/635 A |
| 4,094,914 | 6/1978 | Rottig et al. | 568/862 |
| 4,250,337 | 2/1981 | zur Hausen et al. | 568/853 |
| 4,855,515 | 8/1989 | Morris et al. | 568/862 |
| 4,933,473 | 6/1990 | Ninomiya et al. | 568/862 |
| 5,146,012 | 9/1992 | Salek et al. | 568/861 |

FOREIGN PATENT DOCUMENTS 1017618  1/1966  United Kingdom.

*Primary Examiner*—Rebecca Cook
*Attorney, Agent, or Firm*—William L. Krayer; Robert R. Gavlik

[57] ABSTRACT

Neopentyl glycol is made from isobutyraldehyde and formaldehyde. The formaldehyde may be in the form of paraformaldehyde or aqueous formaldehyde. The aldol reaction product is mixed with a lower alcohol prior to hydrogenation to promote hydrogenolysis and allow recovery of high purity product by simple distillation. In a less preferred mode, the alcohol may be added after hydrogenation, resulting in a smaller improvement over previous processes.

13 Claims, No Drawings

MANUFACTURE OF NEOPENTYL GLYCOL (IV)

RELATED APPLICATIONS

This is a continuation of application Ser. No. 894,961, filed Jun. 8, 1992 (now abandoned), which is a continuation-in-part of Ser. No. 723,097, filed Jun. 28, 1991, entitled "Manufacture of Neopentyl Glycol (III)", now U.S. Pat. No. 5,146,012, issued Sep. 8, 1992, which is a continuation-in-part of Ser. No. 691,927, filed Apr. 26, 1991, entitled "Manufacture of Neopentyl Glycol (I)", now U.S. Pat. No. 5,144,088, issued Sep. 1, 1992 and Ser. No. 716,177, field Jun. 17, 1991, entitled "Manufacture of Neopentyl Glycol (II)", now abandoned.

TECHNICAL FIELD

This invention relates to the manufacture of neopentyl glycol (NPG) from isobutyraldehyde and formaldehyde; in particular, it employs formaldehyde in the form of paraformaldehyde or as an aqueous solution, and is restricted to the use of certain specified steps and conditions, notably the presence of a lower alcohol, in the hydrogenation or distillation of the product of the reaction of formaldehyde and isobutyraldehyde (IBAL).

BACKGROUND ART

Defining Terms: Paraformaldehyde, Aqueous Formaldehyde, and Formaldehyde

Commercially, formaldehyde is available in either of two forms, paraformaldehyde or as an aqueous solution (referred to herein as aqueous formaldehyde). Paraformaldehyde is a crystalline solid consisting of a linear polymeric form of formaldehyde of the molecular formula, $HO(CH_2)_nH$ where n=8–100. Aqueous formaldehyde consists predominently as formaldehyde in its monomeric form. On standing, it will gradually react with itself forming oligomeric formaldehyde and paraformaldehyde. This is commonly inhibited by adding up to 15% methanol as a stabilizer. The term formaldehyde will be used henceforth to designate that either formaldehyde in the form of paraformaldehyde or aqueous formaldehyde is acceptable (or combinations thereof) unless otherwise specified.

In the above-referenced grandparent patent applications, paraformaldehyde is used to react with isobutyraldehyde to make a product comprising in the case of Ser. No. 691,927, now U.S. Pat. No. 5,144,088, hydroxypivaldehyde (HPA), and in Serial No. 716,177, 3-hydroxy-2,2-dimethylpropyl hydroxypivalate. The products are hydrogenated to make NPG. The two applications describe different catalyst systems for the aldol reaction; the hydrogenation step is distinguished primarily by the fact that hydrogenolysis of the indigenous ester impurities is achieved under relatively mild hydrogenation Conditions. By this process, the feed material for hydrogenation, i.e. the reaction product of the aldol step, after dissolution in a suitable alcohol, may be fed directly to the hydrogenation step and the resultant NPG product may be recovered by distillation. As described in Ser. No. 723,097, this was thought to be due in part to the use of paraformaldehyde as the formaldehyde reactant, which greatly reduces the presence of water and avoids other complications, particularly in the generation of waste. The present application is an improvement on the previous inventions, and in the manufacture of NPG generally, in that the present application recognizes that the hydrogenation process described in Ser. No. 723,097, now U.S. Pat. No. 5,146,012 is admirably suited for input streams with or without the presence of significant amounts of water. References which employ copper chromite and other hydrogenation catalysts with the conventional aqueous formaldehyde system which do not teach the addition of a suitable alcohol solvent prior to hydrogenation may be exemplified by U.S. Pat. No. 4,855,515, which recites the historical development of the reaction and emphasizes the use of a particular catalyst in the hydrogenation step. U.S. Pat. No. 3,808,280 discloses the use of triethylamine as a catalyst for the aqueous formaldehyde/isobutyraldehyde reaction.

Paraformaldehyde is used by Snam S.p.A. in UK Patent No. 1,017,618 to react with IBAL in the presence of a tertiary amine to produce a reaction product containing apparently predominantly HPA which may be hydrogenated to NPG. However, the instant invention teaches the addition of a suitable alcohol solvent prior to hydrogenation or distillation which produces a high purity NPG product by simple distillation, obviating the need for additional expensive purification steps.

While zur Hausen et al, U.S. Pat. No. 4,250,337 may use the aldol reaction product directly in their hydrogenation step, they do not use an alcohol in the hydrogenation step to promote hydrogenolysis. As a result of the use of alcohol, our invention achieves high NPG purities together with high yields unlike the aforementioned patent which can only achieve equivalent purities at uneconomical yields.

Other prior art processes which emphasize the hydrogenation step include U.S. Pat. Nos. 4,094,914 to Rottig et al and 4,933,473 to Ninomiya et al. Ninomiya et al especially recognize the formation of the HPA dimer in the aldol reaction product. Rottig et al use alcohols only in a vapor phase hydrogenation which does not include hydrogenolysis, and do not recognize or demonstrate ester hydrogenolysis.

U.S. Pat. No. 4,855,515 claims the use of a manganese promoted copper chromite which allows for efficient hydrogenation at pressures as low as 500 psig in the presence of the amine catalyst and water. However, the product purification is complicated and expensive. The excess IBAL used in the aldol section must be removed before hydrogenation by distillation. After hydrogenation, the effluent must be treated with caustic to saponify the NPG esters and to neutralize amine salts. The sodium salts formed must then be separated from the product before rectification, and an extractive distillation is also necessary to separate recycle IBAL and triethylamine from water, methanol and isobutanol. The purity of the NPG so derived is not specified.

SUMMARY OF THE INVENTION

In the present invention, formaldehyde and IBAL are reacted to make a reaction product which is passed directly to a hydrogenation step including the addition of an alcohol of the formula RR'CHOH wherein R and R' are independently selected from hydrogen and alkyl groups having from 1 to 5 carbon atoms, and together having no more than five carbon atoms, and the thus dissolved product is passed over a suitable hydrogenation catalyst at a pressure of at least 500 psig to about 3000 psig and a temperature of about 100° C. to about 200° C. to recover an NPG product of at least 99% purity by distillation. We prefer to use a hydrogenation feed containing 20 to 90% alcohol and 0–40% water, preferably 30–60% alcohol and 0–20% water, and most preferably 50% alcohol and 1–15% water; the preferred alcohol is methanol. The alcohol may be added after hydrogenation; however, the most benefit is derived from adding the alcohol prior to hydrogenation, which is our preferred mode. In contrast to the concept of parent application 723,097, we now believe the most important aspect of the process is the presence of alcohol regardless of the presence or absence of water during the hydrogenation step.

Our invention will be described in detail in connection with the examples to follow.

DETAILED DESCRIPTION OF THE INVENTION

In the discussion below, it is important to keep in mind the basics of the reactions discussed. First is the aldol reaction:

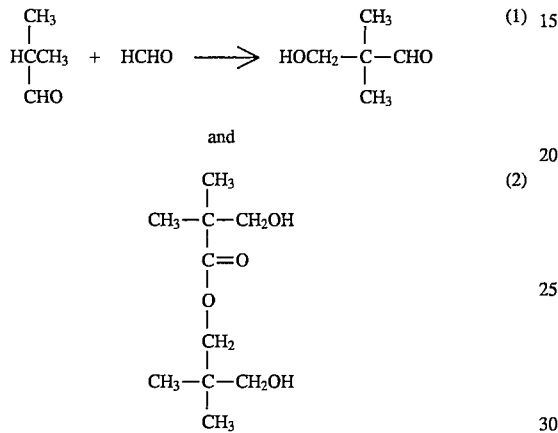

Product (1), which is the major product, is HPA. Product (2) corresponds to 3-hydroxy-2,2-dimethylpropyl hydroxypivalate, which will be referred to herein as "HNHP" which stands for hydroxyneopentyl hydroxypivalate. HNHP is generally a minor product made by the Tishchenko reaction of HPA. In the presence of an appropriate catalyst, pressure, heat and hydrogen, the reaction product including both HPA and HNHP is hydrogenated to form NPG:

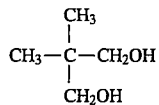

The conventional processes for making NPG by the above route, and which do not add an alcohol in the hydrogenation or distillation step, have the disadvantages of a significant incidence of ester and acid impurities not readily separable from NPG and which must be saponified and neutralized, creating a waste stream, an extraneous extraction step on the waste stream to increase efficiency, and an expensive and complicated purification step. By using the process of our invention, with or without paraformaldehyde, rather than the prior art formaldehyde process, the just-recited disadvantages are obviated. Our process not only avoids these disadvantages but also conducts the hydrogenation step with much greater efficiency. The purity of the NPG product obtained by simple distillation following the teachings of this invention is higher than that obtained by prior art.

Additionally, it has been demonstrated, as will be described herein, that generation of HPA using paraformaldehyde followed by catalytic hydrogenation in an alcoholic solvent can be performed under conditions of hydrogenolysis so that ester impurities are reduced to their corresponding alcohols. NPG product can be obtained from the reduced effluents at >99.5% purity by simple distillation in yields at least comparable to the conventional NPG process using aqueous formaldehyde as described in U.S. Pat. No. 4,855,515.

The high NPG purity of the hydrogenated aldol effluent makes it feasible to eliminate three processing steps: caustic treatment, a distillation or evaporation step such as wiped-film evaporation, and IBAL extraction (see U.S. Pat. No. 4,935,555 to Elias et al). We have produced NPG product in purities greater than 99.5% using this simplified processing scheme. Finally, we have demonstrated to our great surprise that high NPG purities can be achieved at hydrogenation pressures as low as 500 psig $H_2$ using a conventional copper chromite catalyst.

"Specific" Procedure using Paraformaldehyde

A specific reaction using paraformaldehyde may be described as follows: The reaction is performed in a reflux apparatus wherein 1.00 equivalent of IBAL, 1.06 equivalents of paraformaldehyde, and about 0.04 to 0.05 equivalents of triethylamine have been placed under an inert atmosphere. The reaction mixture is stirred at 60°–80° C. for about 5–6 hours or until the reaction is completed. The clear liquid is diluted in a solvent such as methanol and hydrogenated by passing the reaction solution over a conventional copper chromite catalyst at about 160° C. and about 1000 psi. High purity NPG product (>99.5%) is recovered in high yield by distillation.

"Specific" Procedure using Aqueous Formaldehyde

Another specific reaction using aqueous formaldehyde may be described as follows: The reaction is performed in a reflux apparatus wherein 1.00 equivalent of IBAL, 1.00 equivalents of aqueous formaldehyde, and about 0.04 to 0.08 equivalents of triethylamine have been placed under an inert atmosphere. The reaction mixture is stirred at 60°–80° C. for about 2–4 hours or until the reaction is completed. The clear liquid is diluted in a solvent such as methanol and hydrogenated by passing the reaction solution over a conventional copper chromite catalyst at about 160° C. and about 1000 psi. High purity NPG product (>99.5%) is recovered in high yield by distillation.

"General" Procedure using Formaldehyde

More generally, with 1 equivalent of IBAL we may place in a reaction vessel from about 0.5 to about 2 equivalents of formaldehyde and about 0.001 to about 0.1 equivalents (preferably about 0.005 to about 0.1 equivalents) of a tertiary amine catalyst. The reaction mixture is stirred at 60°–80° C. until most of the IBAL is consumed. The resulting solution is diluted in a solvent such as methanol and hydrogenated using a conventional hydrogenation catalyst such as copper chromite. NPG product is obtained by distillation.

We may use various tertiary amines. Specifically, we may use as catalysts any tertiary amines of the general formula $R^1R^2R^3N$ where $R^1$, $R^2$, and $R^3$ are independently selected from alkyl and aryl groups having from one to five carbon atoms and $R^1$ and $R^2$ may form a substituted or unsubstituted cyclic group having from about 5 to about 10 carbon atoms. As is known in the art, if the amine chosen has a boiling point lower than the boiling point (reflux temperature) of IBAL, pressure may be necessary.

Following are several examples of the invention:

EXAMPLE 1

Hydroxyneopentyl hydroxypivalate (HNHP) hydrogenolysis compared to methyl isobutyrate hydrogenolysis:

The following solutions were prepared:

| | | |
|---|---|---|
| (A) | NPG | 47.6 wt. % |
| | HNHP | 2.4 wt. % |
| | triethylamine | 2.3 wt. % |
| | methanol | 47.6 wt. % |
| (B) | methyl isobutyrate | 5 wt. % |
| | methanol | 95 wt. % |

A batch hydrogenation was performed on each solution using 1.4 wt. % stabilized copper chromite at 150° C. for 1 h at 1000 psig $H_2$. Ester hydrogenolysis was monitored. The results follow in Table I. These results are surprising in that the ester impurities indigenous to the process in this invention are more easily hydrogenolyzed than a typical ester such as methyl isobutyrate; they are also surprising in that we are able to hydrogenate easily at relatively low pressures and temperatures. This allows the recovery of high purity NPG product by distillation.

TABLE I

| Ester | % Hydrogenolysis |
|---|---|
| HNHP | 65.7% |
| Methyl isobutyrate | 1.4% |

EXAMPLE 2

Isobutyraldehyde (2000.0 g, 27.74 mol), paraformaldehyde (929.3 g, 29.40 mol), and triethylamine (140.3 g, 1.39 mol) were charged with stirring into a 5L roundbottom flask fitted with a reflux condenser. The apparatus was lowered into a water bath (50° C.). The bath was heated to a temperature of 80° C. over a period of 1.5 h. The reaction was terminated (6 h) and the clear, faintly yellowish aldol effluent was diluted in methanol to make a 50 wt. % aldol in methanol solution. The hydrogenation was performed by passing the methanolic aldol effluent upward through a fixed-bed of stabilized copper chromite at 160° C., 0.5 LHSV, and 1000 psig $H_2$ at >5:1 mole ratio $H_2$:HPA. The results are as shown:

| Components | Hydrogenated Solution (Wt %) | *Neopentyl Glycol Purity |
|---|---|---|
| $CH_3OH$ | 48.79 | |
| IBA | 1.00 | |
| IBacid | 0.00 | |
| TEA | 2.13 | |
| HPA | 0.00 | |
| NPG | 44.93 | 99.67% |
| esters | 0.15 | |
| HNHP | 0.27 | |
| Water | 2.72 | |

IBA = isobutyl alcohol
IBacid = isobutyric acid
TEA = triethylamine
HPA = hydroxypivaldehyde
NPG = neopentyl glycol
esters = e.g., neopentyl glycol monoformate, neopentyl glycol monoisobutyrate
HNHP = hydroxyneopentyl hydroxypivalate
*NPG purities calculated by GC on a "lights-free" ($CH_3OH$, IBA, TEA), "HNHP-free" basis.

In order to demonstrate the effect of various concentrations of alcohol and water during hydrogenolysis, the following experiments were performed, with the results shown in Tables II and III:

EXAMPLE 3

Isobutyraldehyde (1383.0 g, 19.18 mol), paraformaldehyde (670.9 g, 20.33 mol), methanol (349.1 g), and triethylamine (97 g, 0.96 mol) were charged with stirring into a 5L roundbottom flask fitted with a reflux condenser and overhead stirrer. The methanol was added to simulate the methanol contained in the triethylamine recycle stream in a continuous process. The apparatus was held in a water bath (50° C.). After addition of the reagents, the bath was heated to a temperature of 80° C. over a period of 1.5 hours. Over 95% of the IBAL was reacted when the reaction was terminated after 5–½ hours and the clear, faintly yellowish aldol effluent was diluted in methanol to make a 50 wt % aldol in methanol solution. The hydrogenation was performed by passing the methanolic aldol effluent upward through a fixed-bed of stabilized copper chromite at 160° C., 0.5 LHSV, and 1000 psig at a 16:1 mole ratio $H_2$:HPA. The resultant hydrogenation product was batch distilled in a 30-tray Oldershaw column at a 2:1 reflux ratio to recover a high purity neopentyl glycol product. The results are as shown:

| Components | Hydrogenated Solution (Wt %) | Distilled Product (Wt %) |
|---|---|---|
| Methanol | 49.65 | |
| Isobutanol | 1.47 | |
| TEA | 2.15 | |
| NPG | 43.63 | 99.63 |
| esters | 0.26 | 0.37 |
| HNHP | 0.67 | |
| Water | 2.05 | |

TEA = triethylamine
NPG = neopentyl glycol
esters = e.g., neopentyl glycol monoformate, neopentyl glycol monoisobutyrate
HNHP = hydroxyneopentyl hydroxypivalate

EXAMPLE 4

(A) As a control, 1229 g (16.5 mol) of isobutyraldehyde, 1315.0 g (16.2 mol) of 37% aqueous formaldehyde, 96.3 g (0.95 mol) of triethylamine, and 236.7 g of methanol were charged with stirring into a 5L flask equipped with an overhead stirrer and a reflux condenser. The methanol was added for two purposes: maintain the aldol reaction as a single liquid phase and simulate the methanol present due to recycle of the triethylamine stream in a continuous process. The apparatus was held in a water bath at 50° C. After addition of the reagents, the bath was heated to 60° C. Over 95% of the IBAL was converted when the reaction was terminated after 4 hours. The hydrogenation was performed by passing the undiluted aldol effluent upward through a fixed-bed of stabilized copper chromite at 160° C., 1.3 LHSV, and 1000 psig. The resultant hydrogenation product was batch distilled in a 30-tray Oldershaw column at a 2:1 reflux ratio to recover the neopentyl glycol product.

(B) The aldol reaction and hydrogenation described in (A) was repeated except that the hydrogenation effluent was diluted with 2332.4 g of methanol prior to distillation to make a 50 wt % methanol solution. The resultant hydrogenation product was batch distilled in a 30-tray Oldershaw column at a 2:1 reflux ratio to recover the neopentyl glycol product.

The results from the two experiments are summarized in Table II. The data demonstrate the advantage of adding a large amount of an alcoholic solvent after hydrogenation, namely a decrease in neopentyl glycol ester impurities made during the distillation. Without the addition of the alcohol, a much larger amount of neopentyl glycol is converted to impurities.

TABLE II

| Example<br>% Methanol | 4(A)<br>9.5% | 4(B)<br>50%<br>(after hydrogenation) |
|---|---|---|
| Wt % water in hydrogenation | 26.4% | 26.4% |
| Crude NPG Purity* | 98.86% | 98.86% |
| Reaction Selectivity** | 83.26% | 84.66% |
| Total Impurities made*** | 96.01 | 57.88 |
| Product recovery**** | 44% | 65% |

*Crude NPG purity is the purity of the neopentyl glycol product estimated on a "lights-free" (isobutyl alcohol, triethylamine, and methanol) and hydroxyneopentyl hydroxypivalate-free weight % basis.
**Reaction selectivity is the weight percent of neopentyl glycol based on the total IBAL plus formaldehyde reaction products contained in the hydrogenation effluent.
***Total impurities made is the grams per 1000 grams neopentyl glycol of neopentyl glycol esters and HPA side reaction products made during the aldol and hydrogenation reactions and distillation.
****Product recovery is the percent of neopentyl glycol recovered as 99.5% pure product in the distillation.

EXAMPLE 5

(A) The aldol reaction described in Example 4(A) was repeated except that the aldol effluent was diluted with 2332.4 g of methanol prior to hydrogenation rather than following hydrogenation to make a 50 wt % aldol in methanol solution. The hydrogenation was performed by passing the methanolic aldol effluent upward through a fixed-bed of stabilized copper chromite at 160° C., 1.3 LHSV, and 1000 psig. The resultant hydrogenation product was batch distilled in a 30-tray Oldershaw column at a 2:1 reflux ratio to recover high purity neopentyl glycol product.

(B) The aldol reaction described in (A) was repeated except that 2332.4 g of isopropanol was used to dilute the aldol reaction effluent to make a 50 wt % aldol in alcohol solution. The diluted effluent was then hydrogenated at 160° C., 1000 psig, and 1.3 LHSV. The hydrogenation effluent was then batch distilled in a 30-tray Oldershaw column at a 2:1 reflux ratio to recover high purity neopentyl glycol product.

(C) The aldol reaction described in (A) was repeated except that 2332.4 g of n-butanol was used to dilute the aldol reaction effluent to make a 50 wt % aldol in alcohol solution. The diluted effluent was then hydrogenated at 160° C., 1000 psig, and 1.3 LHSV. The hydrogenation effluent was then batch distilled in a 30-tray Oldershaw column at a 2:1 reflux ratio to recover high purity neopentyl glycol product.

The data for the three experiments plus the control from Example 4 are summarized in Table III. The results demonstrate the surprising improvement in neopentyl glycol purity and yields by the addition of a large amount of a suitable alcohol solvent prior to hydrogenation. By following the procedure taught by this invention, the alcohol solvent is used to enhance hydrogenolysis of neopentyl glycol esters as well as undergoing ester interchange to form lower-boiling, easily separable esters. Thus, high purity neopentyl glycol product can be obtained without the need for expensive purification steps such as a caustic treatment. The hydrogenation step described in this improved process would be applicable to an aldol effluent made using either aqueous formaldehyde or paraformaldehyde.

By a suitable alcohol solvent, we mean an alcohol of the formula RR'CHOH wherein R and R' are independently selected from hydrogen and alkyl groups having from one to five carbon atoms. We prefer that the hydrogenolysis feed contain about 20 to 90 wt % alcohol, preferably 30 to 60 wt % alcohol, and most preferably 50 wt % alcohol. The alcohol can be recycled prior to recovering the neopentyl glycol.

TABLE III

| Example<br>Solvent | 4 (A)<br>Control<br>9.5 wt %<br>Methanol | 5 (A)<br>50 wt %<br>Methanol | 5 (B)<br>50 wt %<br>2-Propanol | 5 (C)<br>50 wt %<br>n-Butanol |
|---|---|---|---|---|
| Wt % water in hydrogenation | 26.4% | 14.8% | 14.8% | 14.8% |
| Crude NPG Purity* | 98.86% | 99.67% | 99.70% | 99.29% |
| Distilled NPG Purity | 99.51% | 99.85% | 99.75% | 99.70% |
| Reaction Selectivity** | 83.26% | 93.04% | 91.41% | 89.91% |
| Total Impurities made*** | 96.01 | 20.57 | 27.07 | 49.52 |

*Crude NPG purity is the purity of the neopentyl glycol product estimated on a "lights-free" (isobutyl alcohol, triethylamine, and methanol) and hydroxyneopentyl hydroxypivalate-free weight % basis.
**Reaction selectivity is the percent of neopentyl glycol based on the total IBAL plus formaldehyde reaction products contained in the hydrogenation effluent.
***Total impurities made is the grams per 1000 grams neopentyl glycol of neopentyl glycol esters and HPA side reaction products made during the aldol and hydrogenation reactions and distillation.

EXAMPLE 6

122.9 g of IBAL, 131.5 g of 37% aqueous formaldehyde, 9.6 g of triethylamine, and 23.7 g of methanol were charged with stirring into a flask equipped with a reflux condenser. The apparatus was held in a heated bath at 50° C. After addition of the reagents, the bath was heated to 60° C. The reaction was terminated after 4 hours and the aldol product was diluted with 2317.0 g of methanol to yield a 90 wt % methanol/10 wt % aldol solution. The hydrogenation was performed by passing the methanolic solution upward through a fixed-bed of stabilized copper chromite at 160° C., 1.6 LHSV, and 1000 psig $H_2$. The resultant material was batch distilled to recover the NPG product and the results are as shown:

| Components | Hydrogenated Solution (Wt %) | Neopentyl Glycol Product (Wt %) |
|---|---|---|
| Methanol | 90.38 | |
| Isobutanol | 0.24 | |
| TEA | 0.33 | |
| NPG | 5.78 | 99.60 |
| esters | 0.03 | 0.40 |
| HNHP | 0.05 | |
| Water | 3.17 | |

TEA = triethylamine
NPG = neopentyl glycol
esters = e.g., neopentyl glycol monoformate, neopentyl glycol monoisobutyrate
HNHP = hydroxyneopentyl hydroxypivalate

EXAMPLE 7

Isobutyraldehyde (1106.4 g), paraformaldehyde (536.7 g mol), methanol (279.3 g), and triethylamine (77.6 g) were charged with stirring into a 5L roundbottom flask fitted with a reflux condenser. The methanol was added to simulate the methanol contained in the triethylamine recycle stream in a continuous process. The apparatus was held in a water bath at 50° C. After addition of the reagents, the bath was heated to a temperature of 80° C. over a period of 1.5 hours. The reaction was terminated after 5-½ hours and the aldol effluent was diluted in methanol to make a 50 wt % aldol in methanol solution. An additional 2000 g of water was added to the methanolic solution to increase the total water content to 37.6 wt % (based on the entire feed to the hydrogenation step). The hydrogenation was performed by passing the methanolic aldol effluent upward through a fixed-bed of stabilized copper chromite at 160° C., 1.6 LHSV, and 1000 psig. The resultant hydrogenation product was batch distilled in a 30-tray Oldershaw column at a 2:1 reflux ratio to recover a high purity neopentyl glycol product. The results are as shown:

| Components | Hydrogenated Solution (Wt %) | Neopentyl Glycol Product (Wt %) |
|---|---|---|
| Methanol | 32.36 | |
| Isobutanol | 2.03 | |
| TEA | 1.04 | |
| NPG | 25.31 | 99.53 |
| esters | 0.48 | 0.47 |
| HNHP | 0.70 | |
| Water | 37.65 | |

TEA = triethylamine
NPG = neopentyl glycol
esters = e.g., neopentyl glycol monoformate, neopentyl glycol monoisobutyrate
HNHP = hydroxyneopentyl hydroxypivalate

EXAMPLE 8

1229 g (16.5 mol) of isobutyraldehyde, 1315.0 g (16.2 mol) of 37% aqueous formaldehyde, 96.3 g (0.95 mol) of triethylamine, and 236.7 g of methanol were charged with stirring into a 5L flask equipped with an overhead stirrer and a reflux condenser. The apparatus was held in a water bath at 50° C. After addition of the reagents, the bath was heated to 60° C. The reaction was terminated after 4 hours after which the aldol effluent was diluted with 2332.4 g of methanol to make a 50 wt % methanol solution. The hydrogenation was performed by passing the methanolic aldol effluent upward through a fixed-bed of stabilized copper chromite at 160° C., 1.3 LHSV, and 500 psig. The results are as shown:

| Components | Hydrogenated Solution (Wt %) | Crude Neopentyl Glycol Purity* (GC area %) |
|---|---|---|
| $CH_3OH$ | 44.58 | |
| IBA | 2.48 | |
| IBacid | 0.00 | |
| TEA | 1.43 | |
| HPA | 0.00 | |
| NPG | 24.97 | 99.41 |
| esters | 0.33 | 0.59 |
| HNHP | 0.62 | |
| Water | 25.60 | |

IBA = isobutyl alcohol
IBacid = isobutyric acid
TEA = triethylamine
NPG = neopentyl glycol
esters = e.g., neopentyl glycol monoformate, neopentyl glycol monoisobutyrate
HNHP = hydroxyneopentyl hydroxypivalate
* Neopentyl glycol purity is calculated by gas chromatograph area % on a "lights-free" (methanol, isobutanol, TEA) and "HNHP-free" basis prior to distillation.

We claim:

1. Method of making neopentyl glycol comprising hydrogenating the aldol reaction product of formaldehyde and isobutyraldehyde in the liquid phase at a pressure of about 500–3000 psig, and in the presence of a hydrogenation catalyst and at least about 20 wt % based on the mixture of alcohol and the reaction product, of an alcohol of the formula RR'CHOH wherein R and R' are independently selected from hydrogen and alkyl groups having from one to five carbon atoms and have a total of no more than five carbon atoms, said hydrogenation including the hydrogenolysis of 3-hydroxy-2,2-dimethylpropyl hydroxypivalate and the hydrogenation of hydroxypivaldehyde present in said reaction product.

2. Method of claim 1 wherein the formaldehyde is in the form of paraformaldehyde.

3. Method of claim 1 wherein the formaldehyde is aqueous formaldehyde.

4. Method of claim 1 wherein the reaction of isobutyraldehyde and formaldehyde is conducted in the presence of a catalyst comprising an amine of the formula $R^1R^2R^3N$ where $R^1$, $R^2$, and $R^3$ are independently selected from alkyl and aryl groups having from one to five carbon atoms and $R^1$ and $R^2$ may form a substituted or unsubstituted cyclic group having about 5 to about 10 carbon atoms.

5. Method of claim 1 wherein the alcohol is methanol.

6. Method of claim 1 wherein the hydrogenation reaction is conducted at a temperature of about 100° C. to about 200° C.

7. Method of claim 1 wherein the reaction of isobutyraldehyde with formaldehyde employs a molar ratio of formaldehyde relative to isobutyraldehyde of about 0.5:1 to 2:1.

8. Method of claim 1 wherein the alcohol content of the alcohol-reaction product mixture is no greater than 90% by weight and water is present in an amount no greater than 40% by weight based on the total of reaction product, alcohol and water.

9. Method of claim 1 wherein the alcohol is recovered, the neopentyl glycol is recovered, and the alcohol is recycled.

10. Method of claim 1 wherein the hydrogenation catalyst comprises copper chromite.

11. Method of claim 1 wherein the neopentyl glycol is recovered by distillation.

12. Method of claim i wherein the alcohol is present during the hydrogenation reaction in an amount from about 30% to about 60% by weight of the mixture with aldol reaction product and water is present in an amount from about 0% to about 20% by weight.

13. Method of claim 1 wherein the alcohol is present during the hydrogenation reaction in an amount of about 50% by weight of the mixture with aldol reaction product and water is present in an amount from about 1% to about 15% by weight.

* * * * *